United States Patent [19]

Fischell

[11] Patent Number: 4,628,912

[45] Date of Patent: Dec. 16, 1986

[54] ADJUSTABLE ROOT AND TIP EXTENDERS FOR THE STIFFENER CYLINDER OF A PENILE ERECTION DEVICE

[76] Inventor: Robert E. Fischell, 1027 McCeney Ave., Silver Spring, Md. 20901

[21] Appl. No.: 642,248

[22] Filed: Aug. 20, 1984

[51] Int. Cl.⁴ .............................................. A61F 5/00
[52] U.S. Cl. ...................................................... 128/79
[58] Field of Search .......................................... 128/79

[56] References Cited

U.S. PATENT DOCUMENTS

| | | | |
|---|---|---|---|
| 4,235,227 | 11/1980 | Yamanaka | 128/79 |
| 4,378,792 | 4/1983 | Finney | 128/79 |
| 4,399,812 | 8/1983 | Whitehead | 128/79 |
| 4,411,261 | 10/1983 | Finney | 128/79 |

Primary Examiner—Robert P. Swiatek
Attorney, Agent, or Firm—Kane, Dalsimer, Kane, Sullivan and Kurucz

[57] ABSTRACT

A penile erection prosthesis has a bellows-like adjustable root or tip extender that can be elongated or shortened by adding or deleting fluid from an internal chamber of the extender. By continuously adjusting the amount of fluid added or deleted, the length of the extender can be continuously adjusted. This adjustment can be made either during surgical implant or post-operatively by penetrating the skin with a non-coring needle and entering the extender to add or delete fluid. The length of the implant can be adjusted by adding or deleting fluid either from the root extender or from the tip end extender.

11 Claims, 4 Drawing Figures

U.S. Patent　　　Dec. 16, 1986　　　4,628,912
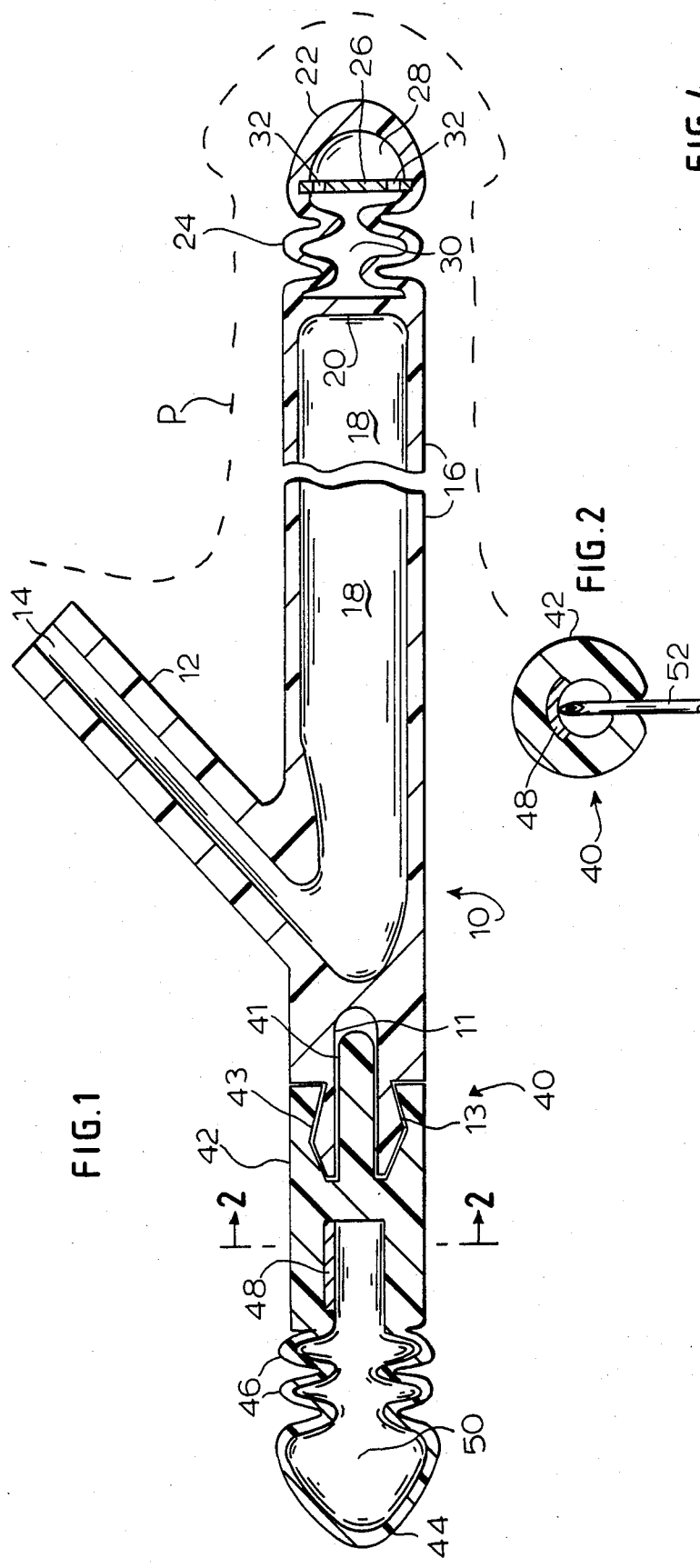
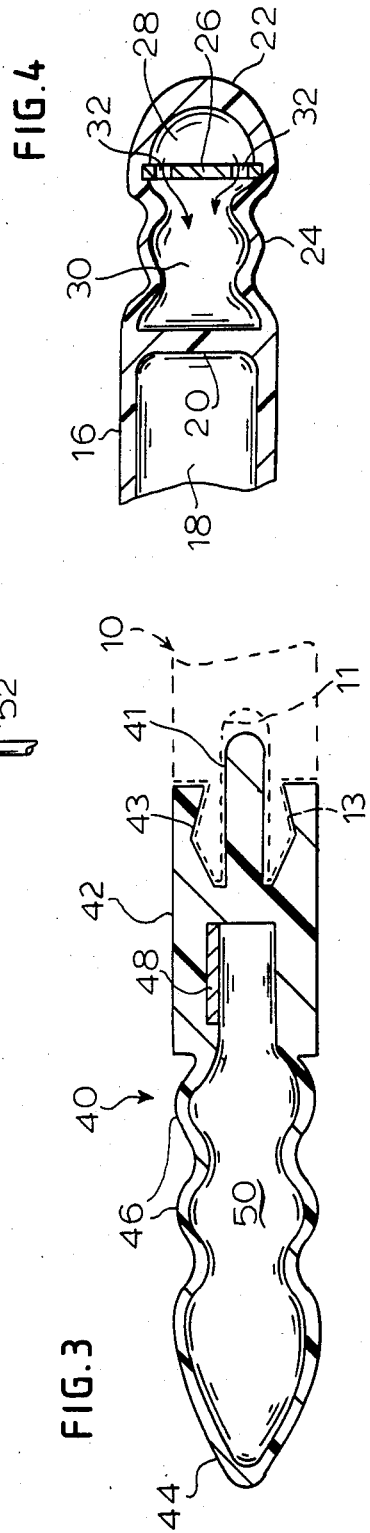

ADJUSTABLE ROOT AND TIP EXTENDERS FOR THE STIFFENER CYLINDER OF A PENILE ERECTION DEVICE

BACKGROUND OF THE INVENTION

1. Field of the Invention

This invention is generally in the field of penile erection devices and more specifically represents an improved means and method for extending the length of a stiffener cylinder which is implanted in the corpus cavernosum of the penis.

2. Description of the Prior Art

For several decades, devices have been invented and implanted in order to provide a penile erection means for men who suffer the affliction of erectile impotence. The earliest of these devices were merely stiff rods (e.g., Barrington, U.S. Pat. No. 4,151,840) which retained their hardness and size at all times. The most successful of these devices, as described by Buuck in U.S. Pat. No. 3,954,102, operate by implanting within the corpus cavernosum of the penis one or more (typically two) stiffener cylinders whose rigidity, when inflated with fluid, provides the desired hardness, stiffness, and increased size for the penis that is necessary for sexual intercourse.

The rigid and semi-rigid (i.e., that can be bent) rods that have been used are typically adjusted in length at the time of surgery to fit exactly within the corpus cavernosum of the penis. In the case of the inflatable stiffener cylinders that are implanted in the corpus cavernosum, it is a common practice for the urological surgeon to place fixed length, root extenders onto the root end of such inflatable cylinders. This is done in order to obtain a total length of the cylinder implant that exactly fills out the corpus cavernosum.

As far as obtaining the exact length required, there are two disadvantages when using the length adjustment methods described above for the rigid and semi-rigid rods and the stiffener cylinder, namely:

1. The root extenders come in finite lengths and therefore do not allow continuous length adjustment, and,
2. No present technique allows for adjusting the implant length after surgical implantation.

SUMMARY OF THE INVENTION

Accordingly, an object of the present invention is to provide a means for extending the length of an inflatable stiffener cylinder prior to implantation to any desired length.

Another object is to provide a means and method for extending the length of a rigid or semi-rigid rod or inflatable stiffener cylinder after it has been implanted into the corpus cavernosum of the penis.

Still another object is to provide the length adjustment within the root of the corpus cavernosum.

A further object is to provide the length adjustment at the tip of pendulous portion of the implanted cylinder within the corpus cavernosum.

Briefly, the invention involves the use of a bellows-like, adjustable root or tip extender that can be elongated or shortened by adding or deleting fluid from an internal chamber of the extender. By continuously adjusting the amount of fluid added or deleted, the length of the extender can be continuously adjusted. This adjustment can be made either during surgical implant or post-operatively by penetrating the skin with a non-coring needle and entering the extender to add or delete fluid. The length of the implant can be adjusted by adding or deleting fluid either from the root extender or from the tip end extender.

BRIEF DESCRIPTION OF THE DRAWINGS

FIG. 1 is a cross sectional view of an inflatable stiffener cylinder showing both an adjustable root extender and an adjustable tip extender.

FIG. 2 is a cross-sectional view of the root extender showing how a non-coring hypodermic needle is used to add or delete fluid.

FIG. 3 is a cross-sectional view of the adjustable root extender with its length considerably extended with the pendulous portion of the stiffener cylinder shown in phantom.

FIG. 4 is a cross-sectional view of the adjustable tip extender with its length considerably extended.

DETAILED DESCRIPTION OF THE INVENTION

In FIG. 1 is shown, a cross-sectional view of an inflatable stiffener cylinder that is implanted in the corpus cavernosum of the penis P which, when filled with a pressurized fluid, can create an erectile state in a normally impotent human male. This stiffener cylinder consists of a pendulous portion 10 and a root portion 40. In fact, the root portion 40 shown in FIG. 1 is an adjustable root extender whose length can be adjusted by adding or deleting fluid.

The pendulous portion 10 consists of a connecting tube 12 whose interior surface 14 typically joins onto some means for filling or emptying the stiffener cylinder in order to obtain respectively the erectile state or the flaccid state. The main portion of the pendulous portion 10 has an outer cylinder wall 16 that joins to the end wall 20 to form a fluid chamber 18.

At the very tip of the pendulous portion 10 is a tip end 22 made of a thick section of silicone rubber. The tip end 22 can be penetrated by a non-coring hypodermic needle (not shown) to add or delete fluid from the inner tip chamber 30. A metal disc 26 (typically made from titanium) is used as a stop for the hypodermic needle that penetrates the tip end 22. The metal disc 26 has several small fluid passageways 32 that are smaller in diameter than the hypodermic needle and allow fluid to pass from the outer tip chamber 28 to the inner tip chamber 30 so as to inflate the chamber 30.

When fluid is added thru the non-coring hypodermic needle, the convolutions 24 are caused to straighten and the length of the adjustable tip extender is increased. When fluid is removed, the tip extender is shortened.

The adjustable root extender 40 shown in FIG. 1 consists of a base 42, a root end 44 and convolutions 46, all of which enclose a root chamber 50. Contained within the base 42 is metal needle stop 48, typically made from titanium. The root portion 40 has an elongated plug 41 that joins the receptacle cavity 11 of the pendulous portion 10 of the stiffener cylinder.

The cross-sectional view at 2—2 in FIG. 1 is shown as FIG. 2. FIG. 2 shows a non-coring hypodermic needle 52 that penetrates the base 42 of the root portion 40 and is stopped from penetrating into the body by the needle stop 48. Thus fluid can be added or deleted from the root chamber 50 to respectively lengthen or shorten the adjustable root extender 40.

FIG. 3 shows the adjustable root extender 40 with its length extended by adding fluid to the root chamber 50 and thus straightening out the convolutions 46. FIG. 3 also shows the plug 41 and an interior surface 43 of the base 42. In this figure, the proximal end of the pendulous portion is shown including the receptacle cavity 11 and an outer surface 13. FIG. 1 shows the plug 41 joined to the receptacle cavity 11 and the inner surface 43 of the root base 42 joined to the outer surface 13 of the pendulous portion 10. This construction forms a mechanical connection that should retain its structural integrity when implanted in the corpus cavernosum. However, silicone adhesive may be used to join the silicone rubber parts of the root extender 40 and the pendulous portion 10. Except for the titanium needle stops, all parts for this implant would preferably be made from medical grade silicone rubber.

The adjustable root extender 40 can be adjusted to any length prior to implantation by the urological surgeon. This is an advantage as compared to fixed length root extenders currently being used because adjustments finer than 1 cm or even ½ cm may be desired for an exact fit into the corpus cavernosum. Furthermore, the needle 52 can be used post-operatively by penetrating the skin to enter the root chamber 50 in order to readjust (typically lengthen) the stiffener cylinder without requiring additional surgery as is now the case when the implanted cylinder is judged to be an incorrect length. In all cases the hypodermic needle 52 is connected to a syringe (not shown) containing a normal saline solution which solution is used to fill the root chamber 50, the inner tip chamber 30 and the outer tip chamber 28. In a manner similar to that described for the root extender, the tip end 22 can be penetrated by a non-coring hypodermic needle to adjust the volume of the inner tip chamber 30 either during or after surgery and thus adjust the length of the pendulous portion 10. FIG. 4 shows the adjustable tip extender, with length extended by adding fluid to the chamber 30 and thus straightening out the convolutions 24.

Although this discussion has centered around extending the root or tip of an inflatable stiffener cylinder, the adjustable root and tip extenders described herein are also readily able to be used for adjusting the length of a penile implant that is a rigid or semi-rigid rod.

Thus the several aforenoted objects and advantages are most effectively attained. Although several somewhat preferred embodiments have been disclosed and described herein, it should be understood that this invention is in no sense limited thereby and its scope is to be determined by that of the appended claims.

What is claimed is:

1. A penile erection prosthesis adapted to be implanted in the corpus cavernosum of the penis comprising in combination:
   a penile implant having a distal end and a proximal end;
   a tip part at the distal end for location in the tip portion of the corpus cavernosum;
   a root portion at the proximal end for location in the root portion of the corpus cavernosum;
   an extension means forming part of at least one of the tip and root, which extension means allows continuous adjustment to any arbitrary length within predetermined limits, which length adjustment is independent of the flaccid or erect state of the prosthesis;
   adjusting the extension means by adjusting the amount of fluid within at least one of the tip part and root part.

2. The invention in accordance with claim 1 wherein the extension means includes a hollow chamber the volume of which is adapted to be selectively adjusted.

3. The invention in accordance with claim 2 wherein the extension means includes a wall having a bellows defining part of the chamber which is adapted to shift in response to adjustment in volume of the chamber.

4. The invention in accordance with claim 3 wherein the wall is penetrable and non-coring by a needle for introducing and removing fluid from the chamber to adjust the volume of the chamber.

5. The invention in accordance with claim 4 wherein a needle stop is disposed within the chamber to limit movement of the needle in the chamber.

6. The invention in accordance with claim 5 wherein both the tip part and the root part include the extension means.

7. The invention in accordance with claim 6 wherein the tip part is integral with the distal end.

8. The invention in accordance with claim 6 wherein the root part is separate from the proximal end of the penile impant having interconnecting means for connecting the root part with the proximal end of the penile implant after the implant has been position in the corpus cavernosum.

9. The invention in accordance with claim 3 wherein the implant includes an inflatable cylinder between the distal end and proximal end and coupling means for coupling the cylinder with a pressurizing source.

10. A method of obtaining length adjustment of a penile erection device comprising the steps of:
    providing a prosthesis adapted to be implanted in the corpus cavernosum of the penis, the penile implant having a distal end and a proximal end, a tip part at the distal end for location in the tip portion of the corpus cavernosum, a root portion at the proximal end for location in the root portion of the corpus cavernosum, an extension means forming part of at least one of the tip and root, which extension means allows continuous adjustment to any arbitrary length within predetermined limits, which length adjustment is independent of the flaccid or erect state of the prosthesis;

11. The method according to claim 10 wherein the adjustment of the extension means is performed after the prosthesis has been inserted in the corpus cavernosum.

* * * * *

UNITED STATES PATENT AND TRADEMARK OFFICE
CERTIFICATE OF CORRECTION

PATENT NO. : 4,628,912
DATED : December 16, 1986
INVENTOR(S) : Robert E. Fischell It is certified that error appears in the above-identified patent and that said Letters Patent is hereby corrected as shown below:

Column 4, claim 1, line 8, delete ";" and insert --.--.

Column 4, lines 9, 10 and 11, delete "adjusting the extension means by adjusting the amount of fluid within at least one of the tip part and root part."

Column 4, claim 8, line 35, delete "position" and insert --positioned--.

Column 4, claim 10, line 54, after ";" insert --adjusting the extension means by adjusting the amount of fluid within at least one of the tip part and root part.--

Signed and Sealed this

Eighth Day of September, 1987

Attest:

DONALD J. QUIGG

*Attesting Officer*   *Commissioner of Patents and Trademarks*